US010682482B2

(12) United States Patent
Baiko et al.

(10) Patent No.: US 10,682,482 B2
(45) Date of Patent: Jun. 16, 2020

(54) FRESH AIR AND ANTI-ASPHYXIATION ASSEMBLY

(71) Applicant: KONINKLIJKE PHILIPS N.V., Eindhoven (NL)

(72) Inventors: Robert William Baiko, Pittsburgh, PA (US); Lauren Patricia Chodkowski, Pittsburgh, PA (US); Marcel Douglas Jaffre, Wendel, PA (US)

(73) Assignee: Koninklijke Philips N.V., Eindhoven (NL)

( * ) Notice: Subject to any disclaimer, the term of this patent is extended or adjusted under 35 U.S.C. 154(b) by 410 days.

(21) Appl. No.: 15/535,417

(22) PCT Filed: Dec. 10, 2015

(86) PCT No.: PCT/IB2015/059496
§ 371 (c)(1),
(2) Date: Jun. 13, 2017

(87) PCT Pub. No.: WO2016/097941
PCT Pub. Date: Jun. 23, 2016

(65) Prior Publication Data
US 2017/0368289 A1      Dec. 28, 2017

Related U.S. Application Data

(60) Provisional application No. 62/092,860, filed on Dec. 17, 2014.

(51) Int. Cl.
*A61M 16/06* (2006.01)
*A61M 16/08* (2006.01)
*A61M 16/20* (2006.01)

(52) U.S. Cl.
CPC ........ *A61M 16/0622* (2014.02); *A61M 16/06* (2013.01); *A61M 16/0666* (2013.01); *A61M 16/0816* (2013.01); *A61M 16/208* (2013.01)

(58) Field of Classification Search
CPC .......... A61M 16/0622; A61M 16/0816; A61M 16/208; A61M 16/06; A61M 16/20; A61M 16/204; A61M 16/206; A61M 16/209
See application file for complete search history.

(56) References Cited

U.S. PATENT DOCUMENTS 4,622,964 A * 11/1986 Flynn ................. A61M 16/0078
128/205.24
5,398,673 A * 3/1995 Lambert ........... A61M 16/0048
128/201.11

(Continued)

FOREIGN PATENT DOCUMENTS

EP        1854494 A1    11/2007
EP        2601994 A2     6/2013

*Primary Examiner* — Timothy A Stanis
*Assistant Examiner* — Margaret M Luarca
(74) *Attorney, Agent, or Firm* — Michael W. Haas

(57) ABSTRACT

An interface device comprises a cushion and a shell coupled thereto which together define an interior space with the face of a user. The shell includes an inlet port structured to have a conduit carrying a flow of treatment gas to the interior space selectively coupled thereto and a first aperture structured to allow the passage of ambient air into the interior space. A first sealing member is operatively coupled to the shell and is positioned such that the first sealing member is movable between a first state in which the first sealing member substantially seals the first aperture, and a second state wherein the sealing member does not substantially seal the first aperture. The first sealing member moves between the first state and the second state responsive to breathing of the patient.

10 Claims, 13 Drawing Sheets

(56) References Cited

U.S. PATENT DOCUMENTS

| | | |
|---|---|---|
| 8,646,449 B2 | 2/2014 | Bowsher |
| 2005/0098183 A1 | 5/2005 | Nash |
| 2009/0260628 A1* | 10/2009 | Flynn, Sr. ......... A61M 16/0078 |
| | | 128/203.28 |

* cited by examiner

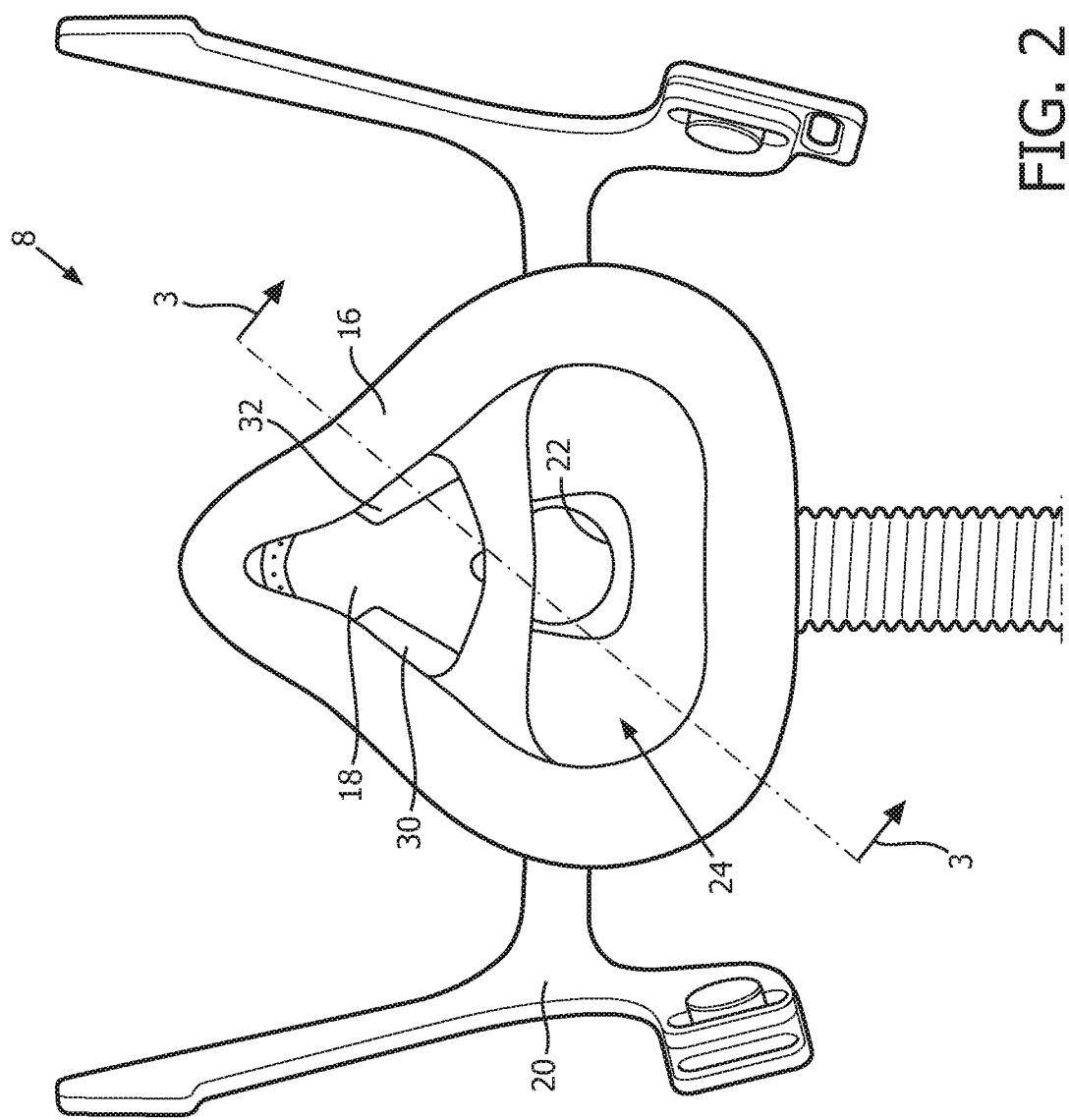

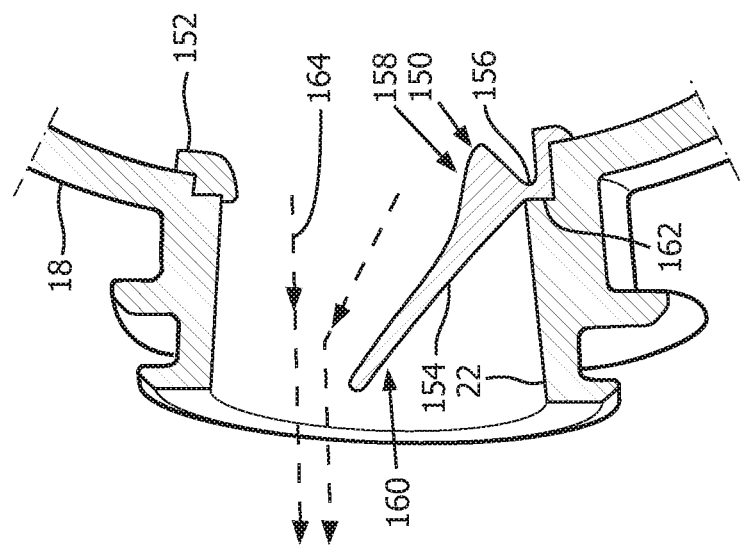
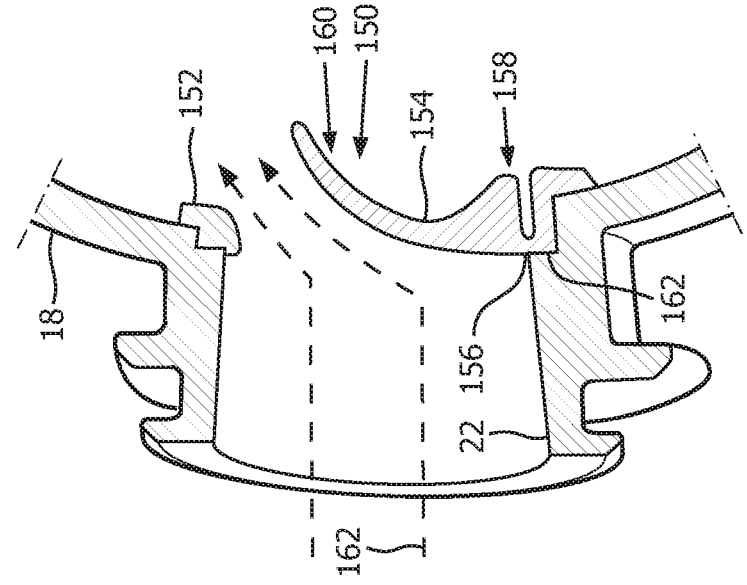
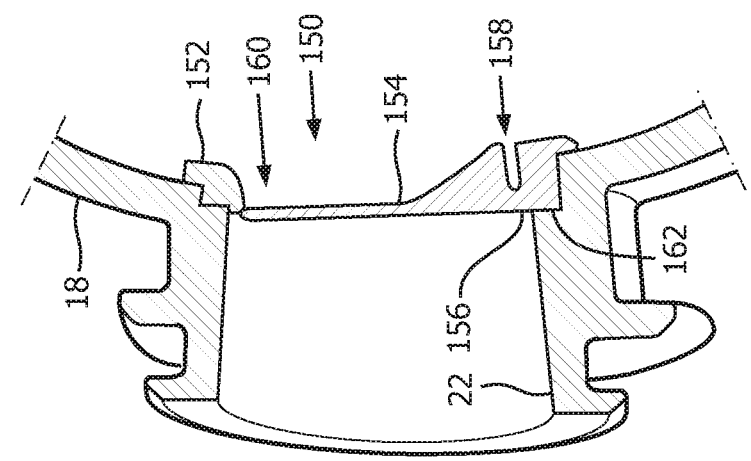

FRESH AIR AND ANTI-ASPHYXIATION ASSEMBLY

CROSS-REFERENCE TO RELATED APPLICATIONS

This patent application claims the priority benefit under 35 U.S.C. § 371 of international patent application no. PCT/IB2015/059496, filed Dec. 10, 2015, which claims the priority benefit under 35 U.S.C. § 119(e) of U.S. Provisional Application No. 62/092,860 filed on Dec. 17, 2014, the contents of which are herein incorporated by reference.

BACKGROUND OF THE INVENTION

1. Field of the Invention

The present invention pertains to systems and devices used in delivering a flow of breathing gas to the airway of a user. More particularly, the present invention systems and components thereof for providing fresh breathing air to a user and handling exhalation gases expelled from a user.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is OSA. Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible cushion on the face of a patient. The mask component may be, without limitation, a nasal mask that covers the patient's nose, a nasal cushion having nasal prongs that are received within the patient's nares, a nasal/oral mask that covers the patient's nose and mouth, or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Anti-asphyxia features (AAF) used in conjunction with OSA therapy are required as a safety device in all masks that cover the nose and mouth. During respiratory therapy, should pressure no longer become available due to a power outage or a pump failure in the ventilator or pressure support device, the patient will continue to be able to breathe with the use of an AAF. Typical designs in the market place take on primarily two configurations.

The first configuration employs a flap style valve typically positioned within the fluid coupling conduit (e.g. elbow connector) of the mask. Such a flap style valve is fundamentally a reed style check valve. As the pressure from the ventilator or pressure support device is applied, the flap style valve opens, allowing air flow to the patient while blocking an exhaust cavity on the opposite side of the flap of the flap style valve. When no pressure comes from the ventilator or pressure support device, the flap seats and allows exhalation and inhalation at atmospheric pressure through a hole to atmosphere. The flap also serves to prevent the patient from pulling air from the volume of air in the gas delivery tubes and the ventilator or pressure support device.

The second configuration employs what is commonly called a Duck-bill valve. Duck bill valves are frequently used in industrial applications where low pressure drops are required. A duck bill valve is fundamentally two symmetrically opposed reed valves (i.e., two symmetrically opposed flaps). As pressure is applied from the ventilator or pressure support device, the two flaps open in opposite directions and seal off exhaust holes provided on each side of the valve. When no pressure comes from the ventilator or pressure support device, the flaps seat with one another and allow exhalation and inhalation at atmospheric pressure through the open exhaust holes. The flap also serves to prevent the patient from pulling air from the volume of air in the gas delivery tubes and the ventilator or pressure support device. A drawback of such designs is the potential for rebreathing of carbon dioxide by the patient resulting from the use of the same exhaust holes for both exhaled air (i.e., carbon dioxide) and inhaled air.

At least two current development trends within the design of masks for non-invasive ventilation and pressure support therapies are impacting the required functionally of supporting components, such as AAF devices, used therewith. These trends are the implementation of smaller gas delivery tubing (e.g., 15 mm inside diameter) and newer, under-the-nose style mask profiles. These features require a balancing of the necessary effective flow area to limit the pressure drop across the AAF while maintaining a smaller package profile. Achieving such balancing has proven to be challenging in connection with AAFs having one of the two prior art configurations described above.

SUMMARY OF THE INVENTION

Accordingly, it is an object of the present invention to provide an interface device that overcomes the shortcomings of conventional interface devices used in, for example, delivering a flow of breathing gas to a user. This object is achieved according to one embodiment of the present invention by providing an interface device comprising: a flexible cushion having a first end adapted to sealingly engage a portion of the face of a user and an opposite second end and a rigid or semi-rigid shell sealingly coupled to the second end of the cushion. The shell and cushion are structured to define an interior space with the face of the user when disposed on the face of the user. The shell includes an inlet port and a first aperture. The inlet port is structured to have a conduit carrying the flow of treatment gas to the interior space selectively coupled thereto, and the first aperture is structured to allow the passage of ambient air into the interior space. The patient interface device further includes a first sealing member operatively coupled to the shell and positioned such that the first sealing member is moveable between (i) a first state in which the first sealing member substantially seals the first aperture, and (ii) a second state in which the first sealing member does not substantially seal the first aperture, and wherein the first sealing member moves between the first state and the second state responsive to breathing of the patient.

The interface device may further comprise a second aperture defined in the shell and a second sealing member operatively coupled to the shell and positioned such that the second sealing member is movable between (i) a first state in which the second sealing member substantially seals the second aperture, and (ii) a second state in which the second sealing member does not substantially seal the second aperture, and wherein the second sealing member moves between the first state and the second state responsive to breathing of the patient. The first sealing member may comprise an integral portion of the cushion. The first sealing member may be disposed in the first state when a pressure within the interior space is at or above ambient pressure and the first sealing member may be disposed in the second state when the pressure within the interior space is less than the ambient pressure. When disposed in the first state, the sealing member may seal against a sealing surface disposed generally parallel to a smooth outer surface of the shell.

When disposed in the first state, the sealing member may seal against a sealing surface disposed at a non-zero angle with respect to a reference line tangent to a smooth outer surface of the shell.

The interface device may further include a valve assembly comprising: a housing having an outer surface and a main passage defined therein. The main passage extends between an inlet defined in the housing and an outlet defined in the housing. The outlet of the housing of the valve assembly is coupled to the inlet port of the shell. The housing further includes a number of sub-passages defined therein, each sub-passage extending between the main passage and an exhaust port defined in the outer surface. The valve assembly further comprises a number of internal sealing members coupled to the housing and disposed in the main passage between the number of sub passages and the inlet. The number of internal sealing members are structured to actuate between (i) a first state wherein the number of internal sealing members substantially seals and segregates the inlet from the outlet and the number of sub-passages, and (ii) a second state wherein the number of internal sealing members substantially seals and segregates the number of sub-passages from the main passage responsive to a flow of gas being provided to the inlet which is greater than a flow of gas being provided to the outlet.

The valve assembly may further comprise a number of external sealing members coupled to the housing about the number of exhaust ports. The number of external sealing members may be structured to actuate between (i) a first state wherein the number of external sealing members substantially seals the number of exhaust ports, and (ii) a second state wherein the number of external sealing members does not substantially seal the number of exhaust ports responsive to a flow of gas being provided to the outlet from the interior space which is greater than a flow of gas being provided to the inlet.

The interface device may further include a resistor mechanism comprising: a mounting portion coupled to the shell about the inlet port and a flap portion coupled to the mounting portion via a hinge portion such that the flap portion is moveable with respect to the mounting portion.

The flap portion may have a thickness which varies from a thickened region near the hinge portion to a thinned region disposed generally away from the hinge portion.

The flap portion may be structured to actuate generally between (i) a first state wherein the flap portion is in a relaxed state and substantially seals the inlet port of the shell; (ii) a second state wherein the thinned portion of the flap portion is displaced toward the interior space responsive to a flow of a breathing gas being provided to the inlet port of the shell; and (iii) a third state wherein the flap portion is displaced away from the interior space responsive to a patient exhaling a flow of exhalation gas and there being no flow of breathing gas provided to the inlet port.

The mounting portion and the flap portion may comprise different portions of a single unitary member.

As another aspect of the invention, a valve assembly as previously described is provided for use in a system delivering a flow of breathing gas to a user.

As yet another aspect of the invention, a method of controlling the flow of inhalation and exhalation gases related to a patient using a patient interface device including a shell having an inlet port provided therein and a cushion coupled thereto is provided. The method comprises: providing a valve in the shell, the valve being structured to selectively permit ambient air to pass through the shell into an interior space defined generally by the shell, cushion and a portion of the patient; and providing a device which restricts a flow of gas into the inlet port.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 2 is a rear elevation view of the patient interface of the system of FIG. 1;

FIG. 12A is a sectional view of the resistor mechanism of FIGS. 10 and 11 taken along line 12-12 of FIG. 10 showing a portion of the mechanism in a relaxed state;

FIG. 12B is a sectional view of the resistor mechanism of FIGS. 10 and 11 taken along line 12-12 of FIG. 10 showing a portion of the mechanism disposed in a position corresponding to when a flow of a breathing gas is provided to the inlet port of the patient interface device; and FIG. 12C is a sectional view of the resistor mechanism of FIGS. 10 and 11 taken along line 12-12 thereof showing a portion of the mechanism disposed in a position corresponding to when a patient is exhaling.

DETAILED DESCRIPTION OF EXEMPLARY EMBODIMENTS

Figure 1:
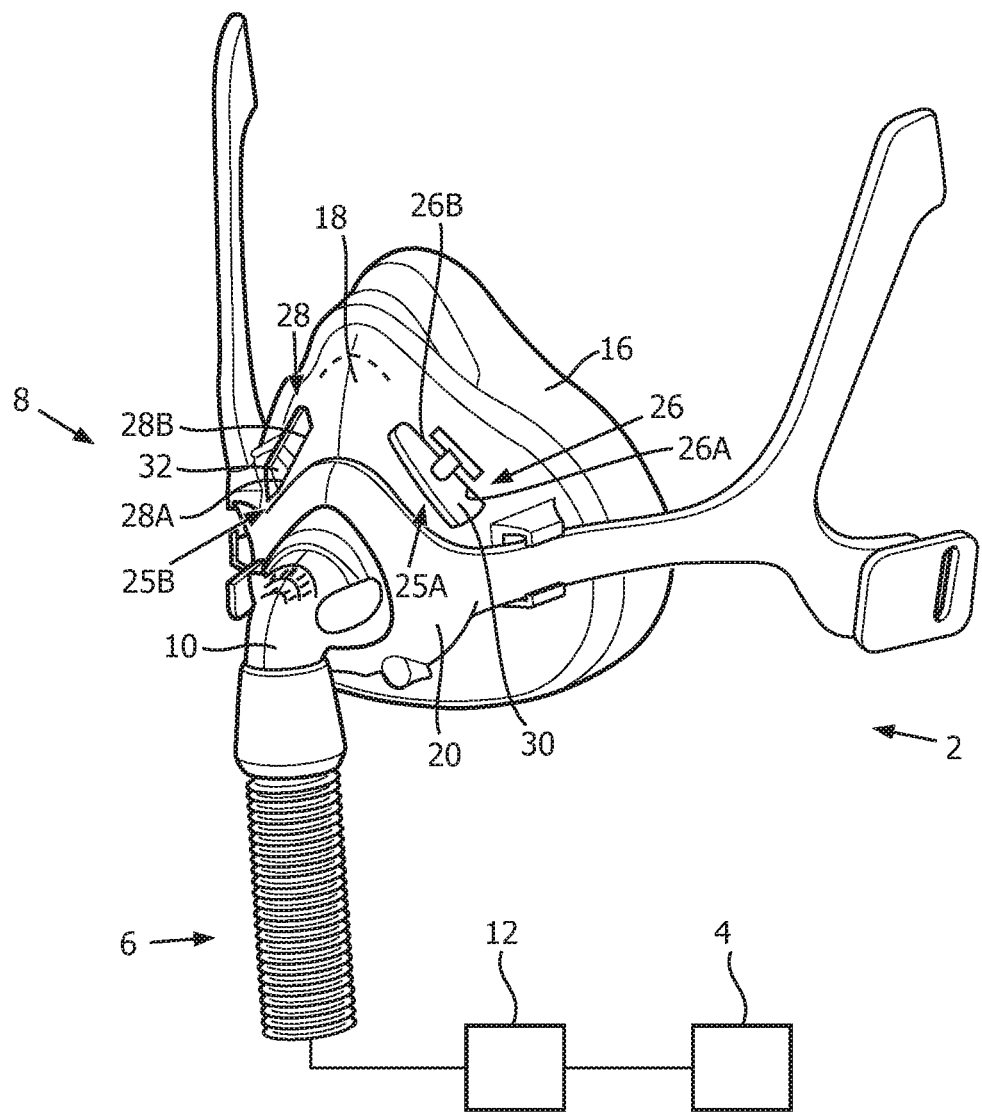
FIG. 1 is a partially schematic diagram of a system adapted to provide a regimen of respiratory therapy to a patient according to one exemplary embodiment of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, the word "number" means one, or any integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 2 adapted to provide a regimen of respiratory therapy to a patient according to one exemplary embodiment of the invention is generally shown in FIG. 1. System 2 includes a pressure generating device 4, a delivery conduit 6, and a patient interface device 8 including an elbow conduit 10. System 2, may optionally include a valve assembly 12 (shown schematically in FIG. 1 and in further detail in FIGS. 7 and 8A-8D) fluidly coupled between pressure generating device 4 and patient interface device 8 as a portion of conduit 6. While in the illustrated embodiment, valve assembly 12 is shown as an independent assembly provided along conduit 6, it will be understood that that is but one possible, exemplary implementation of the present invention. It will thus be appreciated that other, alternative implementations are also possible, such as, without limitation, direct coupling of valve assembly 12 to elbow conduit 10 and conduit 6, integration of valve assembly 12 into elbow conduit 10, or exclusion of valve assembly 12 from system 2.

Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8.

In the exemplary system 2 illustrated in FIG. 1, patient interface 8 is a nasal/oral mask structured to cover the nose and mouth of the patient. However, any type of patient interface device 8 which covers the patient's nose and mouth (e.g., a full face mask) which facilitates the delivery of the flow of breathing gas to, and the removal of a flow of exhalation gas from, the airway of a patient may be used while remaining within the scope of the present invention.

Figure 3A:
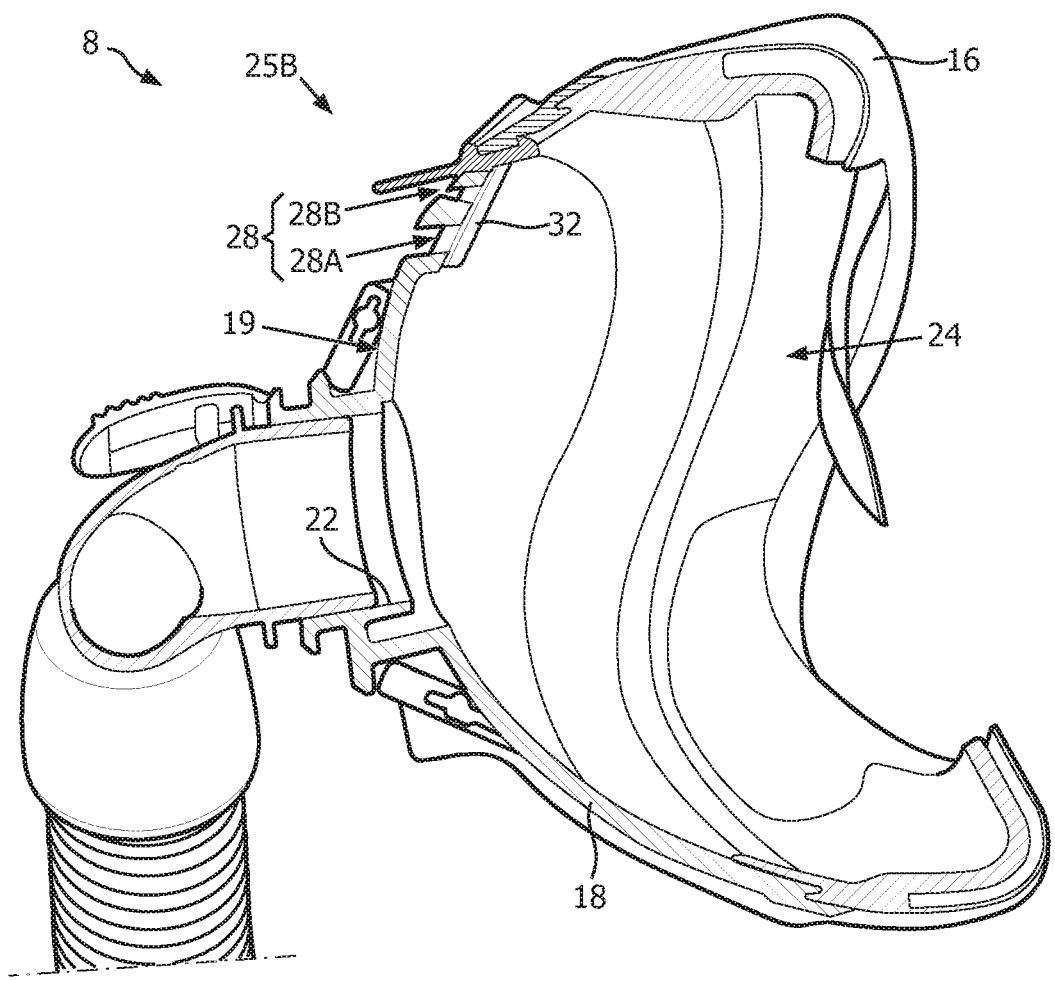
FIG. 3A is a sectional view of the patient interface of FIG. 2 taken along line 3-3 thereof showing a portion of a fresh air inlet assembly according to one exemplary embodiment of the invention disposed in a first state.
Figure 3B:
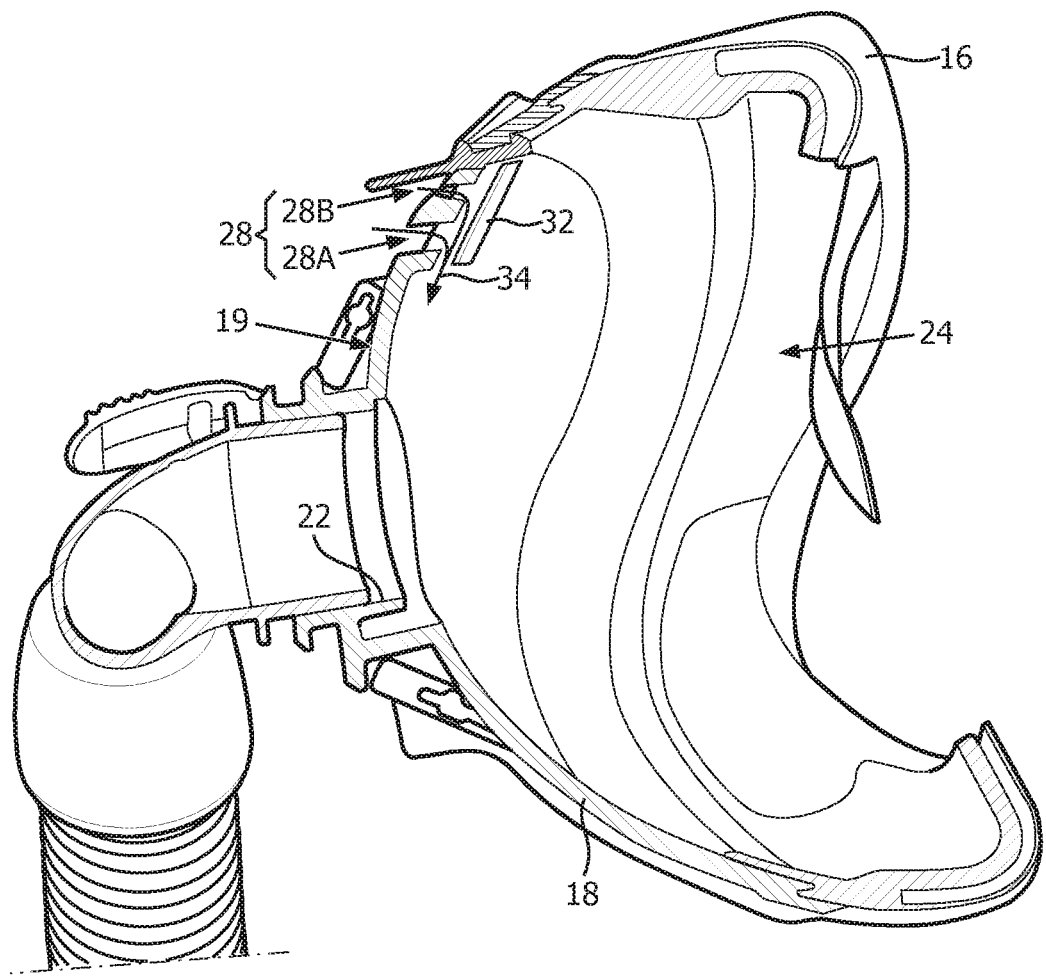
FIG. 3B is a sectional view of the patient interface of FIG. 2 taken along line 3-3 thereof showing a portion of a fresh air inlet assembly according to one exemplary embodiment of the invention disposed in a second state.

Continuing to refer to FIG. 1, and additionally to FIGS. 2, 3A, and 3B, patient interface 8 includes a flexible cushion 16 and a rigid or semi-rigid shell 18. Straps or other portions of a headgear assembly 20 may engage shell 18 or other portions of patient interface device 8 in order to secure patient interface device 8 to the head of a patient. An inlet port 22 (FIGS. 2, 3A, and 3B) in shell 18 to which elbow conduit 10 (FIG. 1) is coupled allows the flow of breathing gas from pressure generating device 4 to be communicated to an interior space 24 (FIGS. 3A and 3B) defined generally by shell 18, cushion 16 and a portion of the face of a patient (not shown) when patient interface device 8 is secured to the patient's face/head. From such interior space 24 the flow of breathing gas then passes to the airway of the patient. As will be described in further detail below, inlet port 22 in shell 18 may also allow for exhalation gas (from the airway of a patient) to be expelled from interior space 24.

Continuing to refer to FIGS. 1, 2, 3A, and 3B, shell 18 further includes a number of fresh air inlet valves for providing for the inlet of ambient air into interior space 24 in the event the flow of breathing gas to interior space is interrupted and or ceased while patient interface device 8 is still secured to a patient. The exemplary embodiment illustrated in FIGS. 1, 2, 3A, and 3B includes two fresh air inlet valves 25A and 25B, however, it is to be appreciated that one or more of the quantity or positioning of such valves may be varied without varying from the scope of the present invention. Each fresh air inlet valve is formed by a number of apertures which pass through shell 18, with each aperture being structured to allow the passage of ambient air from exterior to the patient interface device 8 into the interior space 24. In the exemplary embodiment, fresh air inlet valve 25A is formed in-part by a first set 26 of apertures and fresh air inlet assembly 25B is formed in-part by a second set 28 of apertures, with each set 26, 28 of apertures including two individual apertures 26A, 26B and 28A, 28B. It is to be appreciated, however, that the quantity and/or positioning of the apertures may be varied without varying from the scope of the present invention.

Each fresh air inlet valve further includes a number of sealing members coupled to the shell with each sealing member being disposed adjacent at least one corresponding aperture of the number of apertures. In exemplary embodiments, sealing members formed from silicone with a durometer ranging from 20 A to 60 A were employed. In at least one exemplary embodiment, the sealing members were formed with a slight open bias (generally in the range of from about 5 degrees to about 20 degrees). Such bias lowers the negative pressure threshold thus allowing the sealing members to open very easily upon inhale and resist static charge that sometimes acts on the sealing members while in the closed position. In other embodiments, sealing members formed with no bias have also been employed.

In the exemplary embodiment illustrated in FIGS. 1, 2, 3A and 3B, shell 18 includes two such sealing members, with a first sealing member 30 disposed adjacent the first set 26 of apertures 26A, 26B as a part of fresh air inlet assembly 25A and a second sealing member 32 disposed adjacent the second set 28 of apertures 28A, 28B as a part of fresh air inlet assembly 25B. Each sealing member 30, 32 is structured to actuate generally between (i) a first state wherein the sealing member 30, 32 substantially seals the at least one corresponding aperture responsive to a pressure within the interior space being at or above a certain level, and (ii) a second state wherein the sealing member does not substantially seal the at least one corresponding aperture responsive to the pressure within the interior space 24 being below the certain level.

As an example, the sectional view of FIG. 3A shows a portion of the exemplary embodiment wherein the sealing member 32 of fresh air inlet valve 25B is disposed in the aforementioned first state wherein sealing member 32 substantially seals apertures 28A and 28B of the second set 28 of apertures in a manner such that very little to no air may escape from interior space 24 to the surrounding environment. Sealing member 32 is structured to be in such position when the pressure within the interior space 24 is either at or about the ambient pressure or a pressure higher than the ambient pressure. Such condition wherein the pressure of interior space 24 is greater than the ambient pressure outside interior space 24 would occur when patient interface device 8 is disposed on a patient and (i) a flow of breathing gas is provided to interior space 24 via inlet port 22 (e.g., such as via pressure generating device 4) or alternatively (ii) when there is no flow of breathing gas provided to interior space 24 via inlet port 22 but the patient is exhaling at a rate greater than can exit interior space 24 via inlet port 22 or via other means (e.g., via intentional or unintentional leakage). Such condition in which the pressure of interior space 24 is at or about the ambient pressure would occur when patient interface device 8 is disposed on a patient, there is no flow of breathing gas provided to interior space 24 via inlet port 22, and the patient is (i) exhaling at a rate equal to or less than a rate by which such exhalation gases can exit interior space 24 via inlet port 22 or via other means, is (ii) inhaling at a rate equal to or less than a rate by which gas may be sucked into interior space 24 via inlet port 22 or via other means, or (iii) not inhaling or exhaling.

In contrast to the positioning shown in FIG. 3A, the sectional view of FIG. 3B shows a portion of the exemplary embodiment wherein the sealing member 32 of fresh air inlet valve 25B is disposed in the aforementioned second state wherein sealing member 32 is moved away from, and thus does not substantially seal apertures 28A and 28B of the second set 28 such that ambient air from outside interior space 24 may enter interior space 24, such as shown by arrows 34. Sealing member 32 is structured to be in such position when the pressure within the interior space 24 is less than the ambient pressure. Such condition wherein the pressure of interior space 24 is less than the ambient pressure would occur when patient interface device 8 is disposed on a patient, there is no flow of breathing gas provided to interior space 24 via inlet port 22 and the patient is inhaling at a rate greater than can enter interior space 24 via inlet port 22 or via other means (e.g., intentional leakage via exhalation ports, unintentional leakage between cushion 16 and the patient). Accordingly, it is to be appreciated that the sealing member 32 of fresh air inlet valve 25B will open and shut responsive to breathing of the patient and thus each fresh air inlet valve 25A, 25B generally only provides for the inlet of ambient air in instances where no breathing gas is provided to the patient and thus a patient might asphyxiate if unable to remove patient interface device 8.

Figure 4:
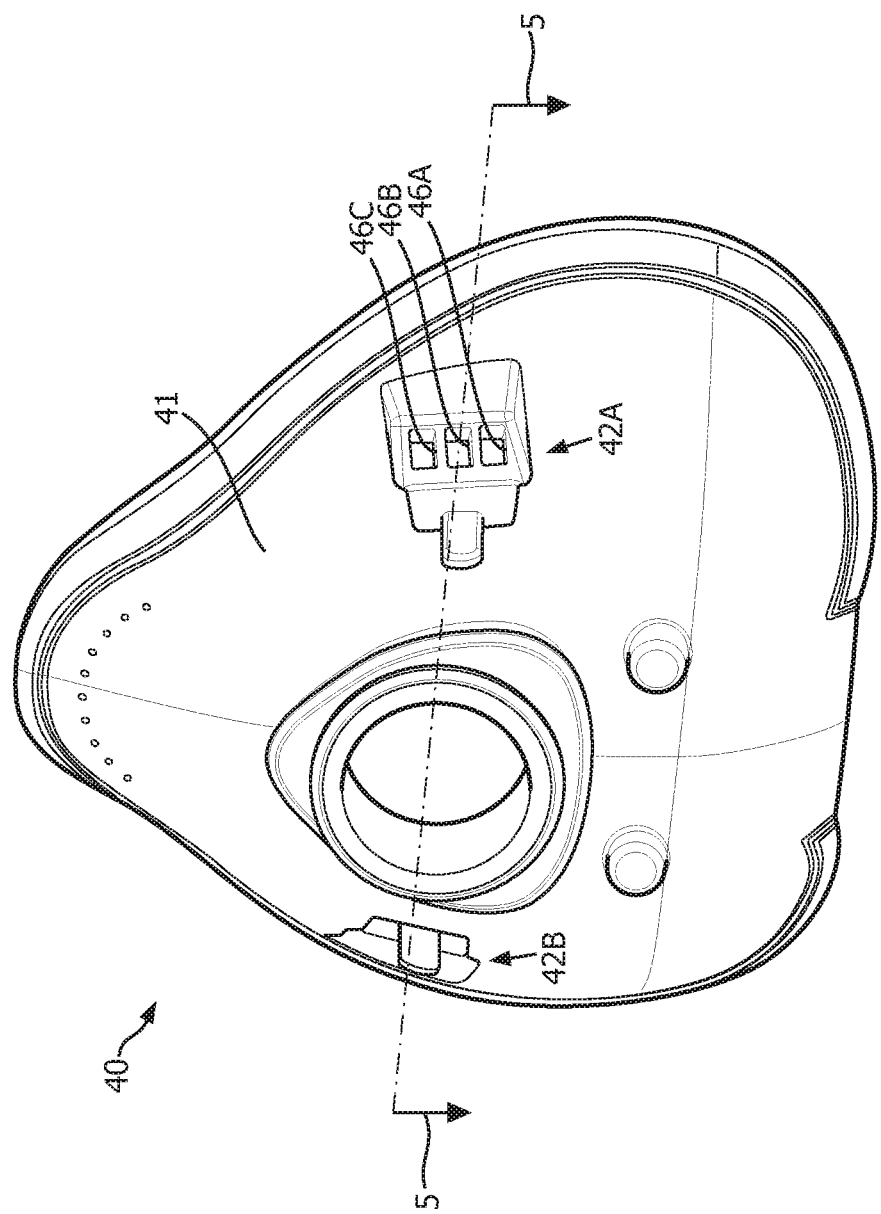
FIG. 4 is an isometric view of a shell according to one exemplary embodiment of the invention for use in a system such as shown in FIG. 1.
Figure 5A:
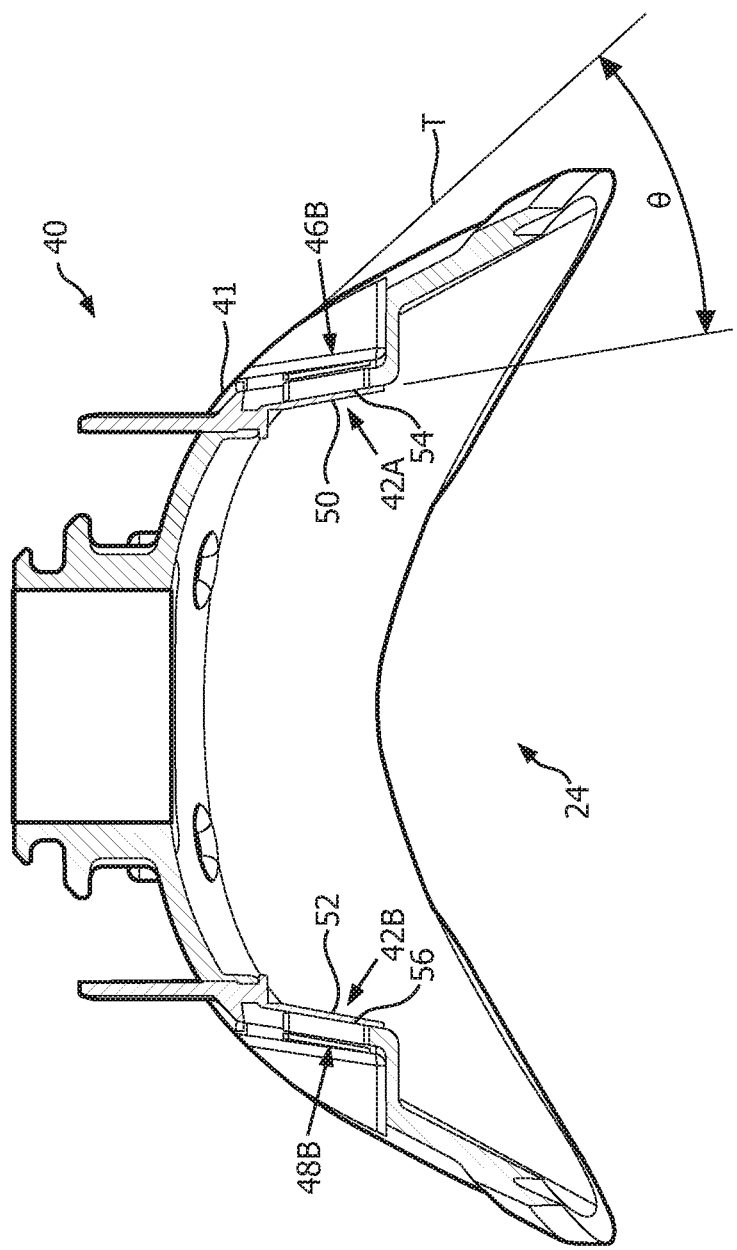
FIG. 5A is a sectional view of the shell of FIG. 4 taken along line 5-5 thereof showing a portion of a fresh air inlet assembly according to one exemplary embodiment of the invention disposed in a first state.
Figure 5B:
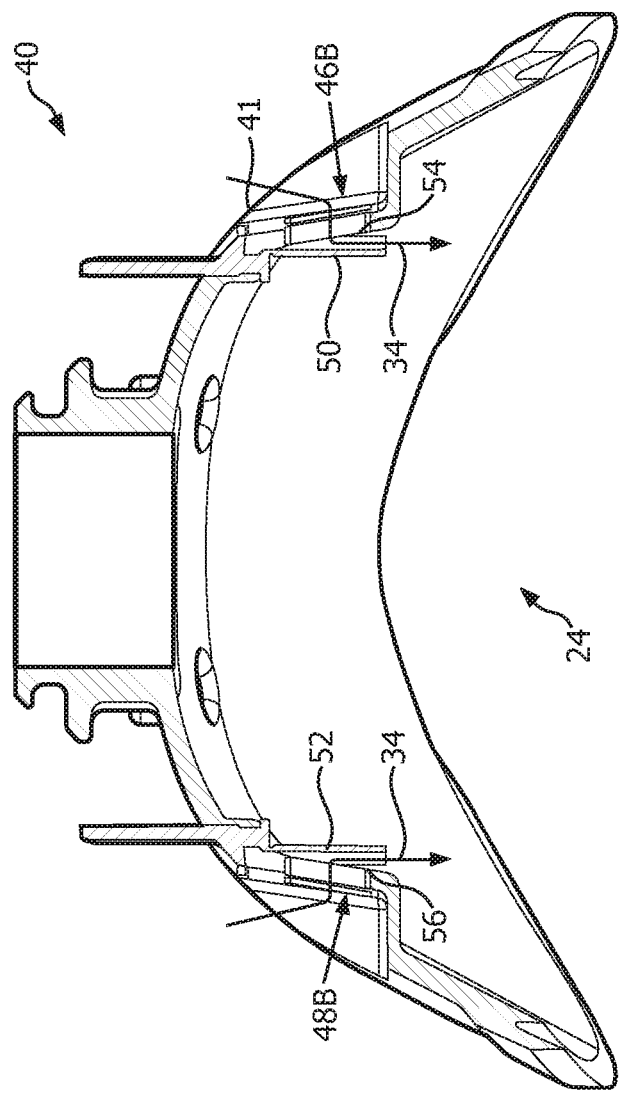
FIG. 5B is a sectional view of the shell of FIG. 4 taken along line 5-5 thereof showing a portion of a fresh air inlet assembly according to one exemplary embodiment of the invention disposed in a second state.

FIGS. 4, 5A and 5B show a shell 40 in accordance with another exemplary embodiment of the present invention which includes a number of fresh air inlet valves 42A and 42B which function in a similar manner as fresh air inlet valves 25A and 25B previously discussed. Accordingly, as shown in FIG. 4, fresh air inlet valve 42A is formed in-part by a first set 46 of apertures including three individual apertures 46A, 46B, 46C. Although not particularly shown in the view of FIG. 4, fresh air inlet valve 42B also includes a second set 48 of three apertures, with only one aperture 48B being illustrated in the sectional views of FIGS. 5A and 5B. Referring to the sectional views of FIGS. 5A and 5B, each fresh air inlet valve 42A, 42B further includes a number of sealing members 50, 52 coupled to shell 40 with each sealing member 50, 52 being disposed adjacent at least one corresponding aperture of the number of apertures, such as apertures 46B and 48B. Unlike the sealing members 30 and 32 of the previously discussed embodiment which seal along a sealing surface (not numbered) disposed generally parallel to the smoothly curved outer surface 19 (FIGS. 3A and 3B) of shell 18, each of sealing members 50 and 52 generally seal along a sealing surface 54, 56 disposed at an angle θ relative to a tangent T to the generally smoothly curved outer surface 41 of shell 40, such as shown in the sectional view of FIG. 5A. In exemplary embodiments of the present invention, angles θ in the range of from about 5 degrees to about 45 degrees have been employed with angles in the range of from about 5 degrees to about 20 degrees being preferred. As with the previous embodiment discussed in regard to FIGS. 1, 2, 3A and 3B, it is to be appreciated that the quantity and/or positioning of the fresh air inlet valves and/or the apertures thereof may be varied without varying from the scope of the present invention.

Figure 6A:
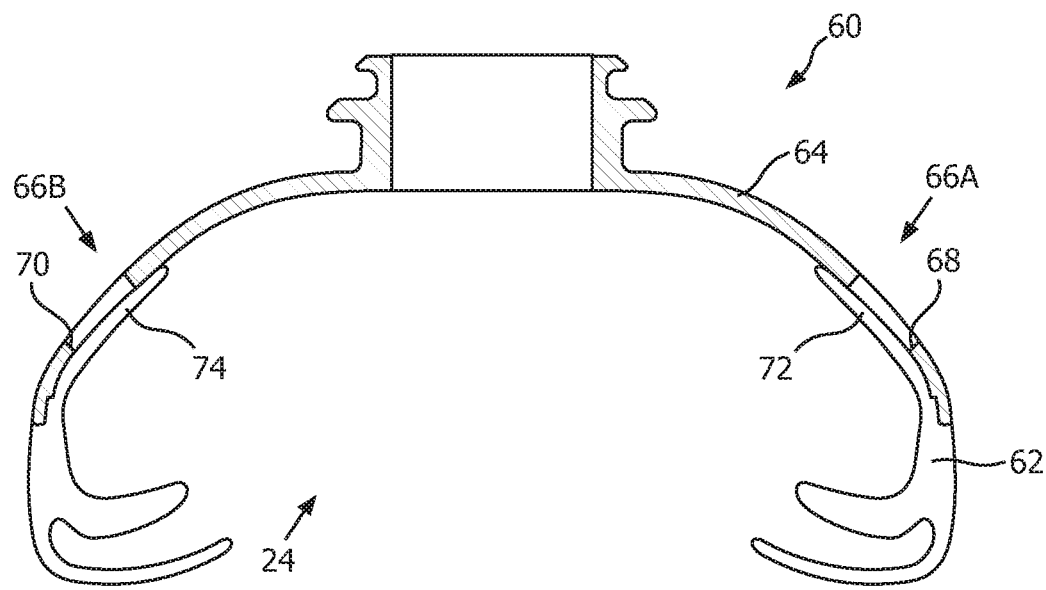
FIG. 6A is a sectional view of a shell showing a sectional view of a fresh air inlet valve according to one exemplary embodiment of the invention with a portion thereof disposed in a first state.
Figure 6B:
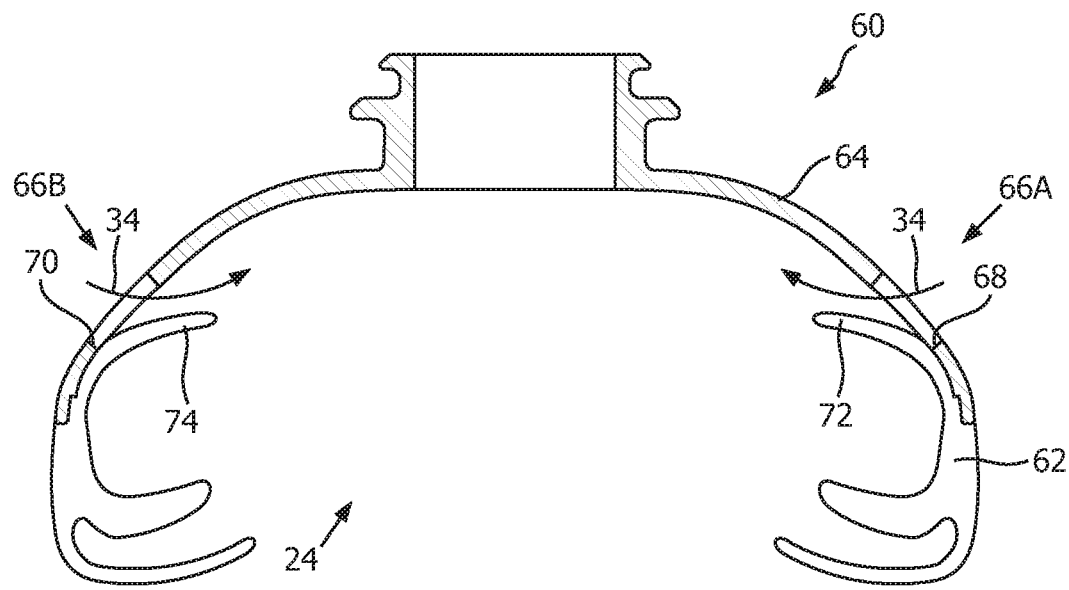
FIG. 6B is a sectional view similar to FIG. 6A but showing a portion of the fresh air inlet valve disposed in a second state.

FIGS. 6A and 6B show sectional views of yet another exemplary embodiment of a patient interface 60 including a flexible cushion 62 coupled to a rigid or semi-rigid shell 64. Shell 64 includes two fresh air inlet valves 66A and 66B, each including an aperture 68, 70 and a sealing member 72, 74 disposed adjacent thereto. Each fresh air inlet valve 66A and 66B functions in a similar manner as the fresh air inlet valves in the embodiments previously described. However, unlike the fresh air inlet valves previously described which included individually formed sealing members which were individually coupled to a shell, each sealing member 72, 74 of fresh air inlet valves 66A and 66B is formed as an integral portion of the cushion 62. Such arrangement offers a number of advantages. For example, such arrangement requires only a single manufacturing operation as the sealing members are formed in the same process as the facial sealing element of the cushion. In contrast, the sealing elements in the earlier described embodiments require several extra steps (molding the elements and inserting/coupling each element to the shell). This embodiment also removes the element of human error in inserting the sealing elements in the proper orientation.

Figure 7A:
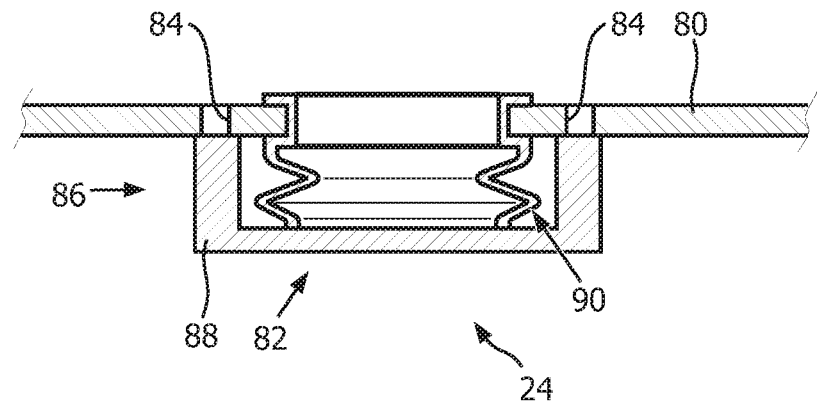
FIG. 7A is a sectional view of a shell showing a sectional view of a fresh air inlet valve according to one exemplary embodiment of the invention with a portion thereof disposed in a first state.
Figure 7B:
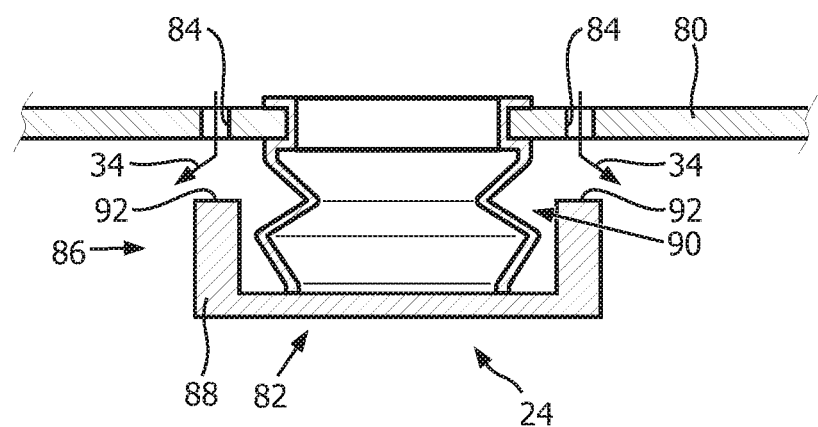
FIG. 7B is a sectional view similar to FIG. 7A but showing the portion of the fresh air inlet valve disposed in a second state.

FIGS. 7A and 7B show sectional views of a shell 80 including another exemplary embodiment of a fresh air inlet valve 82. Similar to the other exemplary fresh air inlet valves previously discussed, fresh air inlet valve 82 includes a number of apertures 84 passing through shell 80 and a sealing member 86 having a generally rigid or semi-rigid sealing portion 88 coupled to shell 80 via a connection portion 90. Sealing portion 88 is preferably formed from any rigid or semi-rigid material (e.g., polycarbonate, nylon, harder silicones, and TPEs) or other suitable material and may be formed separately from, or integrally with, connection portion 90. The contacting sealing surface(s) 92 of sealing portion 88 can differ from the remainder of sealing portion 88 to provide for an enhanced seal (e.g., like a gasket) and can be, for example, without limitation, a softer silicone. Connection portion 90 may be formed from a silicone or other suitable material. In exemplary embodiments, materials ranging in hardness from 5 shA to 60 shA have been employed. As shown in the embodiment illustrated in FIGS. 7A and 7B, connection portion 90 may be formed as a bellows-like structure disposed in/coupled to an aperture (not numbered) formed in shell 80. It is to be appreciated, however, that connection portion 90 may be coupled to shell 80 via other suitable arrangements (which also provide for venting of air from within the bellows-like portion) without varying from the scope of the present invention. It is also to be appreciated that other suitable arrangements which provide for similar movement of sealing portion 88 toward and away from shell 80 as described below may also be employed without varying from the scope of the present invention.

Sealing member 86 is moveable between a first state in which each of aperture 84 is generally sealed by sealing member 86 (such as shown in FIG. 7A) and a second state in which each aperture 84 is not sealed by sealing member 86 and thus ambient air from outside an interior space 24 defined in-part by shell 80 (similar to as previously discussed) may enter interior space 24, such as shown by arrows 34. Movement between such states occurs in a similar manner as the embodiments of the fresh air inlet valves previously described.

Having thus described several exemplary embodiments of patient interfaces or portions thereof including fresh air inlet valves in accordance with the present invention, a number of other features of the present invention will now be described which may be used independently or in conjunction a fresh air inlet valve in accordance with the present invention.

Figure 8:
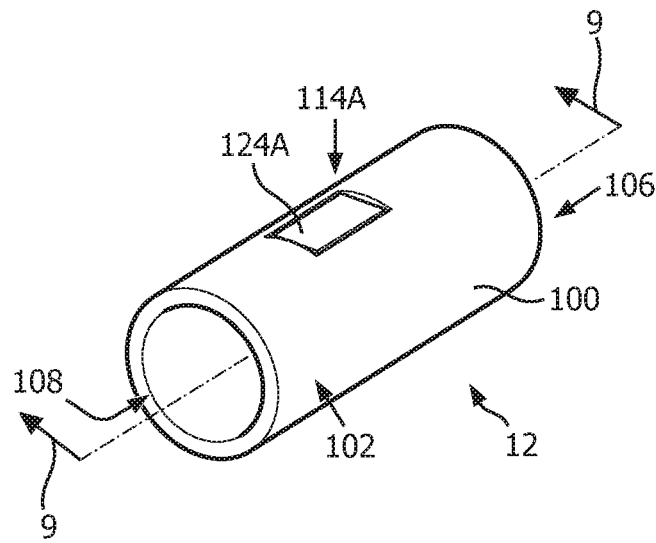
FIG. 8 is an isometric view of a valve assembly such as shown schematically in the system of FIG. 1.

Referring to FIG. 8, an isometric view of an exemplary embodiment of the valve assembly 12 from the system 2 of FIG. 1 is shown. Referring to the sectional views of FIGS. 9A-9C, valve assembly 12 includes a housing 100 having an outer surface 102 and a main passage 104 defined therein. In exemplary embodiments, housing 100 was formed from a rigid polycarbonate material, although housing 100 may be formed from one or more other suitable materials without varying from the scope of the present invention. Main passage 104 extends between an inlet 106 and an outlet 108 defined in housing 100. Although shown as a generally straight passage, it is to be appreciated that main passage 104 may be disposed along a non-straight pathway (e.g., without limitation, bent, angled, etc.) without varying from the scope of the present invention. Housing 100 adjacent each of inlet 106 and outlet 108 is structured to be coupled to a conduit or other member such as via a silicone or thermoplastic elastomer (TPE) cuff or other suitable arrangement. Housing 100 further includes a number of sub-passages 112A and 112B defined therein, with each sub-passage 112A, 112B extending between main passage 104 and an exhaust port, shown generally at 114A and 114B, defined in outer surface 102 of housing 100.

Figure 9A:
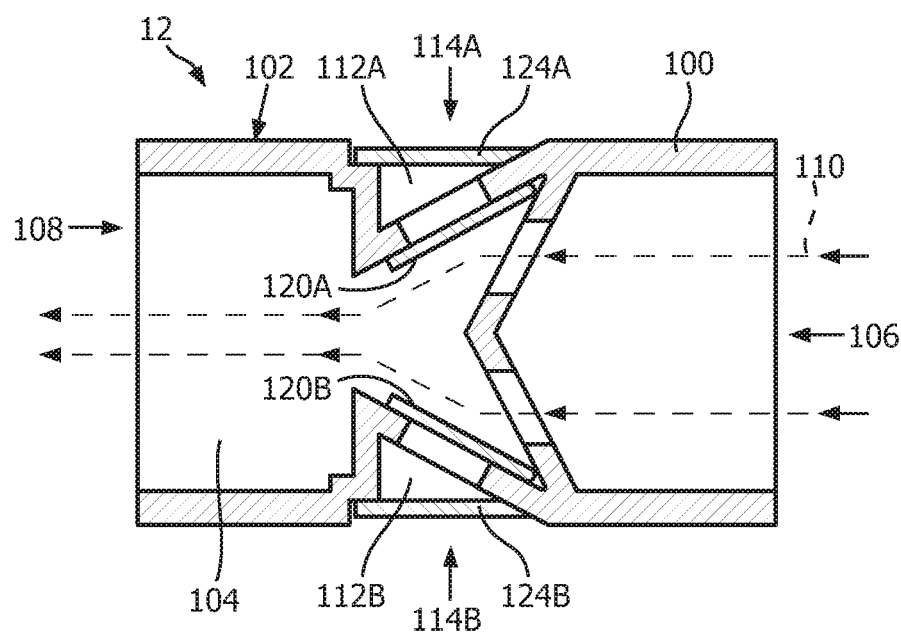
FIG. 9A is a sectional view of the valve assembly of FIG. 8 taken along line 9-9 thereof showing portions of the valve disposed in positions corresponding to when a flow of breathing gas is provided to an inlet thereof.
Figure 9B:
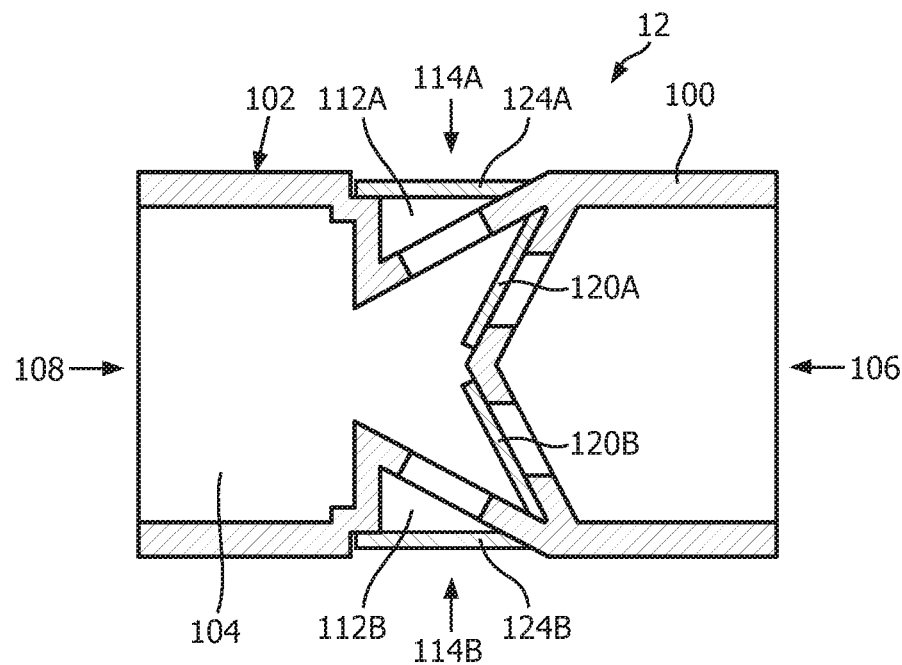
FIG. 9B is a sectional view of the valve assembly of FIG. 8 taken along line 9-9 thereof showing portions of the valve disposed in positions corresponding to when there is no flow of a breathing gas provided to the inlet thereof and a patient using an interface device coupled to an outlet thereof is either inhaling or not exhaling.
Figure 9C:
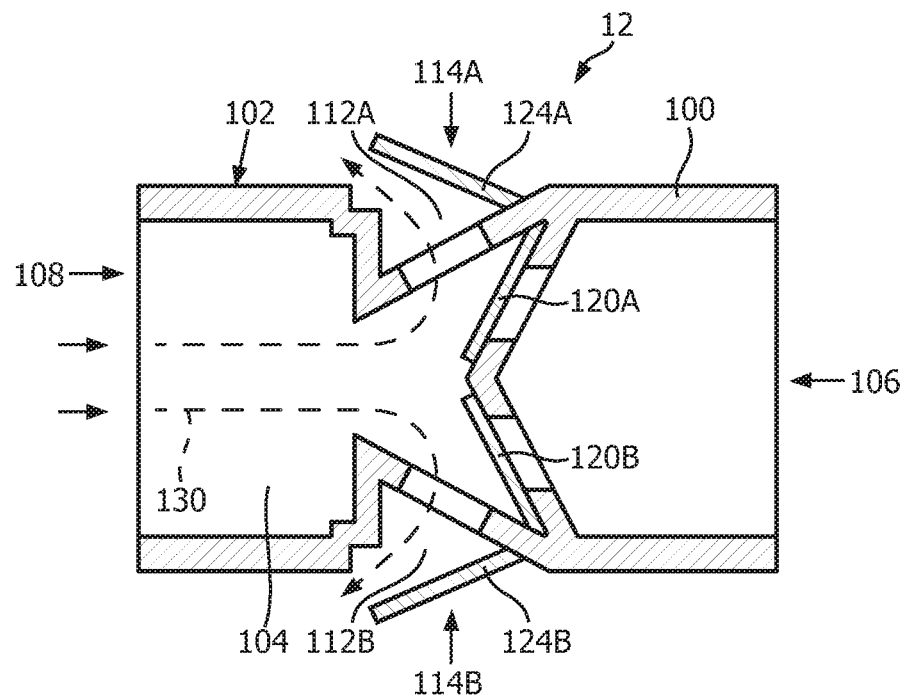
FIG. 9C is a sectional view of the valve assembly of FIG. 8 taken along line 9-9 thereof showing portions of the valve disposed in positions corresponding to when there is no flow of a breathing gas provided to the inlet thereof and a patient using an interface device coupled to the outlet thereof is exhaling.

Continuing to refer to FIGS. 9A-9C, valve assembly 12 further includes a number of inner sealing members 120A and 120B disposed in main passage 104 between the number of sub passages 112A and 112B and inlet 106. In exemplary embodiments of the present invention, each inner sealing member was formed from silicone ranging in hardness from 20 sHA to 40 sHA, although other suitable materials may be employed without varying from the scope of the present invention. The number of inner sealing members 120A and 120B are coupled to housing 100 and are structured to actuate between (i) a first state (such as shown in FIGS. 9B and 9C) wherein the number of inner sealing members 120A and 120B substantially seals and segregates inlet 106 from outlet 108 and the number of sub-passages 112A and 112, B, and (ii) a second state (such as shown in FIG. 9A) wherein the number of inner sealing members 120A and 120B substantially seals and segregates the number of sub-passages 112A and 112B from main passage 104 responsive to a flow of gas (shown by dashed lines 110 in FIG. 9A) being provided to inlet 106 which is greater than a flow of gas provided to outlet 108 such that gas flows from inlet 106 to outlet 108. Each inner sealing member 120A, 120B is biased in the range of 0 to 3 cm $H_2O$ toward the first state (4 cm $H_2O$ is generally the lowest threshold for therapy pressure), the purpose of which will be fully appreciated with the further discussion below.

Valve assembly 12 further includes a number of outer sealing members 124A, 124B coupled to housing 100 about the number of exhaust ports 114A, 114B. Each of the outer sealing members may be formed from the same or a similar material as the inner sealing members. As also shown in FIGS. 9A-9C, the number of outer sealing members 124A and 124B are structured to actuate between (i) a first state (such as shown in FIGS. 9A and 9B) wherein the number of outer sealing members 124A and 124B substantially seals the number of exhaust ports 114A and 114B, and (ii) a second state (such as shown in FIG. 9C) wherein the number of outer sealing members 124A and 124B does not substantially seal the number of exhaust ports 114A and 114B. Such actuation from the first state to the second state occurs when a flow of gas (such as shown by dashed lined 130 in FIG. 9C) is provided to outlet 108 of housing 100 which is greater than a flow of gas provided to inlet 106 of housing.

Having thus described the basic structure of an exemplary embodiment of a valve assembly 12, the operations of such a valve and the components thereof employed in an exemplary system will now be discussed in conjunction with the system shown in FIG. 1. When employed in system 2, inlet 106 is coupled to pressure generating device 4 and outlet 108 is coupled to patient interface device 8 such that when pressure generating device 4 is producing a flow of breathing gas, such flow of breathing gas passes through main passage 104 of valve assembly 12 (such as shown by dashed arrows 110 in FIG. 9A) and on to patient interface device 8. Accordingly, during such time the inner sealing members 120A and 120B are disposed in their second state (as previously described) while the outer sealing members 124A and 124B are disposed in their first state (as previously described).

If the flow of breathing gas from pressure generating device 4 ceases to be provided to inlet 106 (e.g., due to failure of device 4 or disconnection from device 4), the inner sealing members 120A and 120B return to their first state (as previously described), such as shown in FIGS. 9B and 9C, thus segregating and sealing off inlet 106 from outlet 108 and sub-passages 112A and 112B. During such time, outer sealing members 124A and 124B are disposed in their first state (see FIG. 9B, as previously described) unless/until a patient using patient interface device 8 exhales, thus producing a flow of breathing exhaust gas into outlet 108 which causes outer sealing members 124A and 124B to be actuated to their second state (see FIG. 9C, as previously described) thus allowing the flow of breathing exhaust gas to exit valve assembly 12 (and thus system 2) via the number of sub-passages 112A, 112B and exhaust ports 114A, 114B (such as shown by dashed arrows 130 in FIG. 9C). Once the flow of breathing exhaust gas ceases (i.e., the patient stops exhaling), the outer sealing members 124A and 124B return to their first state (such as shown in FIG. 9B), thus sealing exhaust ports 114A, 114B and prohibiting air external to valve assembly 12 from entering. During such time when the flow of breathing gas from pressure generating 4 is not being provided to patient interface device 8, the patient is able to inhale ambient air through the number of fresh air inlet valves 25A and 25B provided in shell 18.

Accordingly, it is to be appreciated that during normal operation of such a system 2 wherein a flow of breathing gas is being provided to the patient, valve assembly 12 acts merely as a portion of the conduit communicating the flow of breathing gas from the pressure generating device 4 to the patient interface device 8 and fresh air inlet valves 25A and 25B remain in the closed sealed positions. However, in the event the flow of breathing gas from pressure generating device 4 ceases for whatever cause, valve assembly 12 acts to block the flow path to the pressure generating device 4 from the patient interface device 8 and provides a pathway for exhaust gases exhaled from a patient to be expelled from system 2 while inhibiting outside air from being inhaled into the system. Additionally, the bias of inner sealing members 120A and 120B toward their first state (i.e. when such members segregate/seal inlet 106 from outlet 108) acts to prevent the patient from potentially inhaling gas trapped between valve assembly 12 and pressure generating device 4. Instead, fresh ambient air may be inhaled by the patient through one or more of the fresh air inlet valves provided in shell 18 which are spaced from the first location, thus avoiding contaminating the incoming fresh air with the outgoing exhaust gases.

Figure 10:
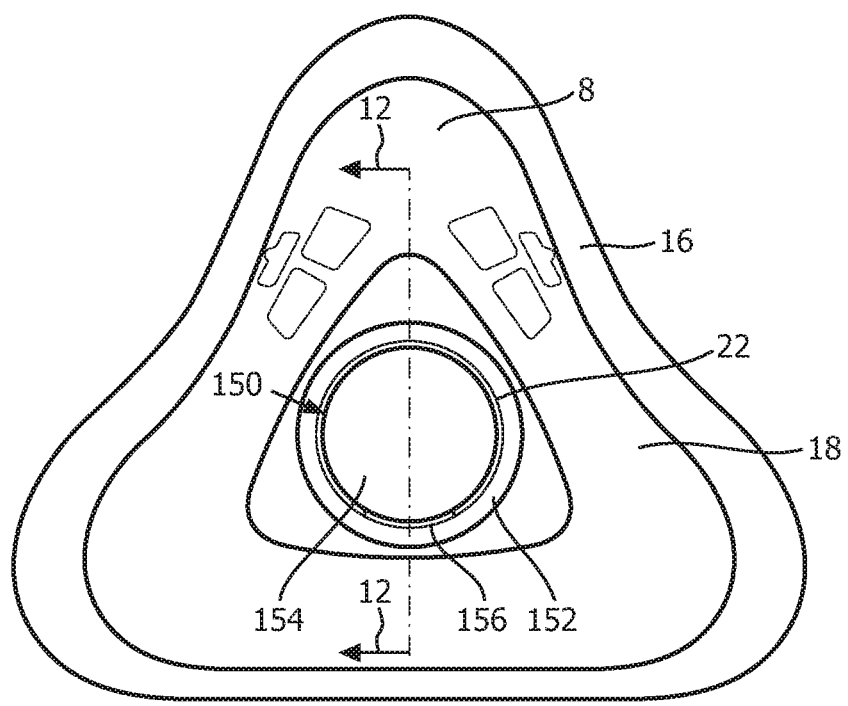
FIG. 10 is an elevation view of a front side of a patient interface including a resistor mechanism according to one exemplary embodiment of the invention.
Figure 11:
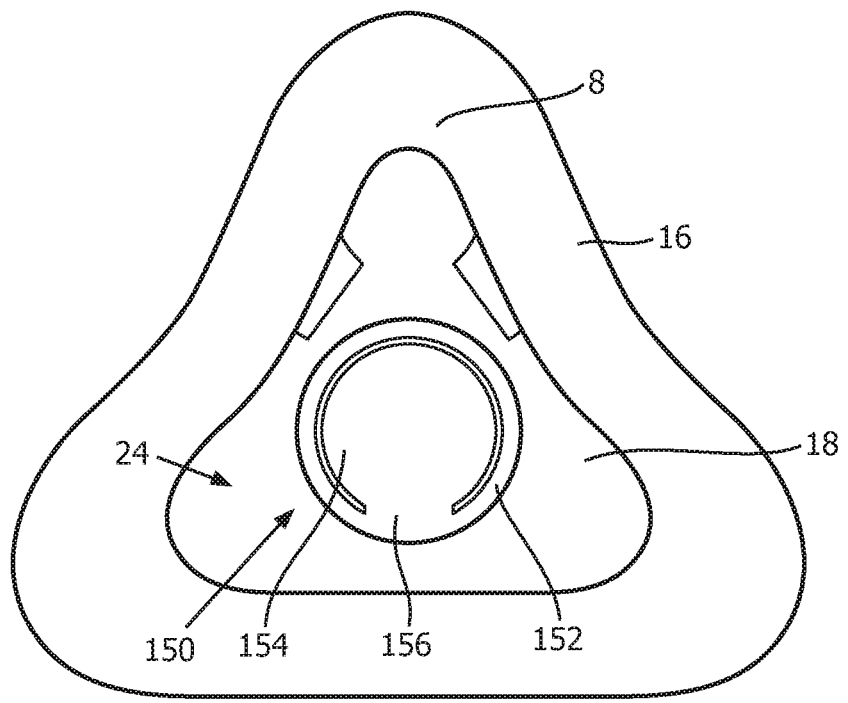
FIG. 11 is an elevation view of a patient side of the patient interface including a resistor mechanism of FIG. 10.

FIGS. 10, 11 and 12A-12C show an exemplary embodiment of another feature of the present invention, particularly a resistor mechanism 150 which may be used in conjunction a fresh air inlet valve in accordance with the present invention. FIG. 10 shows a front elevation view a patient interface device 8 such as previously described in conjunction with FIGS. 1, 2, 3A and 3B having a resistor mechanism 150 installed in, or adjacent to, inlet port 22 of shell 18. Resistor mechanism 150 includes a mounting portion 152 and a flap portion 154 coupled thereto via a hinge portion 156 such that flap portion 154 is moveable with respect to mounting portion 152, as discussed in greater detail below. Although shown having only a single flap portion 154, it is to be appreciated that the quantity of flap portions employed may be varied without varying from the scope of the present invention. Mounting portion 152 may be coupled to shell 18 via a frictional fit within inlet port 22, such as shown in the illustrated embodiment, via an adhesive, or via any other suitable means or combination thereof. As shown in the illustrated exemplary embodiment, mounting portion 152 and flap portion 154 may be formed as different portions of a single unitary member. In other embodiments, mounting portion 152 and flap portion 154 may be formed separately and then subsequently bonded together. In one exemplary embodiment, mounting portion 152 was formed from a bonding silicone that was molded in place. In another exemplary embodiment, mounting portion 152 was formed as a rigid piece (e.g., polycarbonate, polypropylene) that snaps to the shell. In exemplary embodiments, flap portion 154 was formed from a silicone material ranging in durometer from 20 A to 60 A.

As shown in the sectional views of FIGS. 12A-12C, flap portion 154 has a thickness which varies from a thickened region 158 near hinge portion 156, to a thinned region 160 disposed generally away from hinge portion 156. In the exemplary embodiment shown in FIGS. 12A-12C, hinge portion 156 is generally offset toward an outer edge 162 of mounting portion 152 which provides for generally the entirety of flap portion 154 to be readily moveable in a direction generally away from a patient. In contrast, movement of flap portion 154 toward a patient is generally restricted by an interaction between thickened region 158 and mounting portion 152 such that only thinned region 160 is generally moveable, via flexure of flap portion 154, toward a patient.

Referring to the sectional views of FIGS. 12A-12C, the flap portion 154 of resistor mechanism 150 is structured to actuate generally between (i) a first state, such as shown in FIG. 12A, wherein flap portion 154 is in a relaxed state and substantially seals inlet port 22 of shell 18; (ii) a second state, such as shown in FIG. 12B, wherein thinned portion 160 of flap portion 154 is displaced toward a patient responsive to a flow of breathing gas, such as shown by arrows 162 in FIG. 12B, provided to inlet port 22 such as by a pressure generating device 4 (previously described in connection with FIG. 1); and (iii) a third state, such as shown in FIG. 12C, wherein flap portion 154 is disposed away from a patient responsive to a patient exhaling a flow of exhalation gas, such as shown by arrows 164 in FIG. 12C, and there being no flow of breathing gas provided to inlet port 22.

Having thus described the basic structure of an exemplary embodiment of a resistor mechanism 150, the operations of such a mechanism and the components thereof employed in an exemplary system will now be discussed in conjunction with a system similar to that shown in FIG. 1 except without a valve assembly 12 as resistor mechanism 150 generally takes the place of such a valve assembly. When employed in system 2, mounting portion 152 is coupled to/in inlet port 22 of shell 18. Pressure generating device 4 is coupled to patient interface device 8 via conduit 6 such that when pressure generating device 4 is producing a flow of breathing gas, such flow of breathing gas deforms thinned portion 160 of flap portion 154 of resistor mechanism 150 toward the patient (i.e., into its second state) and flows into interior space 24 (such as shown by arrows 162 in FIG. 12B). If the flow of breathing gas from pressure generating device 4 ceases to be provided to inlet port 22 (e.g., due to failure of device 4 or disconnection from device 4), thinned portion 160 of flap portion 154 returns to its relaxed, first state, such as shown in FIG. 12A, thus generally sealing off inlet port 22. If a patient using patient interface device 8 exhales while there is no flow of breathing gas being provided to inlet port 22, resistor flap 154 is actuated away from the patient (i.e., into its third state) thus allowing a flow of breathing exhaust gas (such as shown by arrows 164 in FIG. 12C) to exit interior space 24 and enter into conduit 6). When the patient ceases exhaling, flap portion 154 returns to its relaxed, first state.

Accordingly, it is to be appreciated that during normal operation of such a system 2 wherein a flow of breathing gas is being provided to the patient, resistor mechanism only slightly impedes the flow of breathing gas into interior space 24. However, in the event the flow of breathing gas from pressure generating device 4 ceases from whatever cause, resistor mechanism 150 acts to block the flow path to the pressure generating device 4 from the patient interface device 8 and provides essentially a one-way check-valve which provides for exhaust gases exhaled from a patient to be readily expelled from interior space 24 into conduit 6 while generally inhibiting gas from within conduit 6 from being inhaled into interior space 24 (as the pressure required to deform thinned portion 160 flap portion 154 toward the patient is greater than the pressure needed to actuate the sealing members of fresh air inlet valves 25A and 25B). Instead, fresh ambient air may be inhaled by the patient through one or more of the fresh air inlet valves provided in shell 18. Hence such arrangement provides fresh air to the patient while also isolating exhaust gases exhaled by the patient.

While the present invention has been described in connection with a patient interface device used to treat, for example, a patient suffering from OSA, it will be understood that that is meant to be exemplary, and that the principles of the present invention can be can also be applied in connection with other face masks applications where concern for asphyxia may occur, such as, without limitation, anesthesia delivery masks or general use face masks where patients may be unable to manipulate a mask to maintain breathing. Furthermore, as the valve assembly embodiments described herein actuate upon very basic fluid dynamic principles, they may also be used in industrial applications, for example, and without limitation, as a combination check valve/bleed-off valve where air circulation may require access to atmosphere if direct system pressure is not applied.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An interface device for use in delivering a flow of breathing gas to a user, the interface device comprising:
    a flexible cushion having a first end adapted to sealingly engage a portion of the face of a user and an opposite second end;
    a rigid or semi-rigid shell sealingly coupled to the second end of the cushion, the shell and cushion are structured to define an interior space with the face of the user when disposed on the face of the user, the shell including an inlet port and a first aperture, wherein the inlet port is structured to have a conduit carrying the flow of treatment gas to the interior space selectively coupled thereto, and wherein the first aperture is structured to allow the passage of ambient air into the interior space; and
    a first sealing member operatively coupled to the shell and positioned such that the first sealing member is movable between (i) a first state in which the first sealing member substantially seals the first aperture, and (ii) a second state in which the first sealing member does not substantially seal the first aperture, and wherein the first sealing member moves between the first state and the second state responsive to breathing of the patient, wherein the first sealing member is formed as an integral portion of the cushion.

2. The interface device of claim 1, further comprising a second aperture defined in the shell and a second sealing member operatively coupled to the shell and positioned such that the second sealing member is movable between (i) a first state in which the second sealing member substantially seals the second aperture, and (ii) a second state in which the second sealing member does not substantially seal the second aperture, and wherein the second sealing member moves between the first state and the second state responsive to breathing of the patient.

3. The interface device of claim 1, wherein the first sealing member is disposed in the first state when a pressure within the interior space is at or above ambient pressure and wherein the first sealing member is disposed in the second state when the pressure within the interior space is less than the ambient pressure.

4. The interface device of claim 1, wherein when disposed in the first state the first sealing member seals against a sealing surface disposed generally parallel to a smooth outer surface of the shell.

5. The interface device of claim 1, wherein when disposed in the first state the first sealing member seals against a sealing surface disposed at a non-zero angle (θ) with respect to a reference line (T) tangent to a smooth outer surface of the shell.

6. The interface device of claim 1, further comprising a valve assembly comprising:
   a housing having an outer surface and a main passage defined therein, the main passage extending between an inlet defined in the housing and an outlet defined in the housing, the housing further including a number of sub-passages defined therein, each sub-passage extending between the main passage and an exhaust port defined in the outer surface; and
   a number of internal sealing members coupled to the housing and disposed in the main passage between the number of sub passages and the inlet, the number of internal sealing members being structured to actuate between (i) a first state wherein the number of internal sealing members substantially seals and segregates the inlet from the outlet and the number of sub-passages, and (ii) a second state wherein the number of internal sealing members substantially seals and segregates the number of sub-passages from the main passage responsive to a flow of gas being provided to the inlet which is greater than a flow of gas being provided to the outlet, wherein the outlet of the housing of the valve assembly is coupled to the inlet port of the shell.

7. The interface device of claim 6, wherein the valve assembly further comprises a number of external sealing members coupled to the housing about the number of exhaust ports, the number of external sealing members being structured to actuate between (i) a first state wherein the number of external sealing members substantially seals the number of exhaust ports, and (ii) a second state wherein the number of external sealing members does not substantially seal the number of exhaust ports responsive to a flow of gas being provided to the outlet from the interior space which is greater than a flow of gas being provided to the inlet.

8. The interface device of claim 1, further comprising a resistor mechanism comprising:
   a mounting portion coupled to the shell about the inlet port; and
   a flap portion coupled to the mounting portion via a hinge portion such that the flap portion is moveable with respect to the mounting portion.

9. The interface device of claim 8, wherein the flap portion has a thickness which varies from a thickened region near the hinge portion to a thinned region disposed generally away from the hinge portion, and wherein the flap portion is structured to actuate generally between (i) a first state wherein the flap portion is in a relaxed state and substantially seals the inlet port of the shell; (ii) a second state wherein the thinned portion of the flap portion is displaced toward the interior space responsive to a flow of a breathing gas being provided to the inlet port of the shell; and (iii) a third state wherein the flap portion is displaced away from the interior space responsive to a patient exhaling a flow of exhalation gas and there being no flow of breathing gas provided to the inlet port.

10. The interface device of claim 9, wherein the mounting portion and the flap portion comprise different portions of a single unitary member.

* * * * *